United States Patent [19]

Schulz et al.

[11] Patent Number: 4,923,503

[45] Date of Patent: May 8, 1990

[54] AGENTS FOR INFLUENCING PLANT GROWTH

[75] Inventors: Guenter Schulz; Ernst Buschmann, both of Ludwigshafen; Hubert Sauter, Mannheim; Bernd Zeeh, Limburgerhof; Bruno Wuerzer, Otterstadt; Johann Jung, Limburgerhof; Guenter Retzlaff, Roemerberg, all of Fed. Rep. of Germany

[73] Assignee: BASF Aktiengesellschaft, Ludwigshafen, Fed. Rep. of Germany

[21] Appl. No.: 677,034

[22] Filed: Nov. 30, 1984

[30] Foreign Application Priority Data

Dec. 1, 1983 [DE] Fed. Rep. of Germany ....... 3343415

[51] Int. Cl.$^5$ .............................................. A01N 31/41
[52] U.S. Cl. ...................................................... 71/92
[58] Field of Search ............................................ 71/92

[56] References Cited

U.S. PATENT DOCUMENTS 4,124,767 11/1978 Mixich et al. ........................ 548/341
4,771,065 7/1989 Kraner et al. ........................ 514/383

FOREIGN PATENT DOCUMENTS 104726 4/1984 European Pat. Off. .
0119572 12/1984 European Pat. Off. .
2431407 12/1982 Fed. Rep. of Germany .

OTHER PUBLICATIONS

Synthetic Metals, vol. 4 (1981), pp. 119–113.
Journal of Polymer Science, vol. 20 (1982).

Primary Examiner—Richard L. Raymond
Attorney, Agent, or Firm—Keil & Weinkauf

[57] ABSTRACT

Agents for influencing plant growth, containing as active ingredient an azolylacetophenone oxime ether of the formula

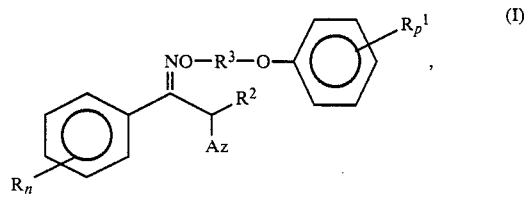

where R and $R^1$ independently of one another are each hydrogen, halogen, alkyl, cycloakyl, alkoxy, alkylthio, alkylsulfonyl, haloalkyl, nitro, cyano, phenyl or phenoxy, $R^2$ is hydrogen, alkyl, aralkyl, allyl or propargyl, $R^3$ is a divalent radical of the formula —$(CH_2)_m$—, —$(CH_2CH_2O—)_uCH_2CH_2$—, —$(CH_2)_vCH=CH—(CH_2)_t$— or —$(CH_2)_v—C\equiv C—(CH_2)_t$—, n, p, u, v and t independently of one another are each 1, 2 or 3, m is an integer from 2 to 10, and Az is 1,2,4-triazol-1-yl, pyrazol-1-yl or imidazol-1-yl, or a salt or metal complex thereof, and a method of influencing plant growth or of destroying unwanted plants with these active ingredients.

4 Claims, No Drawings

AGENTS FOR INFLUENCING PLANT GROWTH

The present invention relates to agents which are based on azolylacetophenone oxime ethers and which influence the growth of plants or act as herbicides.

It has been disclosed that azolylacetophenone oxime ethers can be used as fungicides (German Laid-Open Application No. DOS 2,431,407). Bioregulator, plant growth regulator or herbicidal activity of such oxime ethers is unknown to date.

We have found that azolylacetophenone oxime ethers of the formula (I)

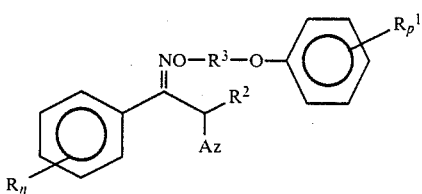

where R and $R^1$ independently of one another are each hydrogen, halogen, alkyl, cycloalkyl, alkoxy, alkylthio, alkylsulfonyl, haloalkyl, nitro, cyano, unsubstituted or substituted phenyl or unsubstituted or substituted phenoxy, $R^2$ is hydrogen, alkyl, aralkyl or unsubstituted or substituted allyl or is propargyl, $R^3$ is a divalent radical of the formula $-(CH_2)_m-$, $-(CH_2CH_2O-)_uCH_2CH_2-$, $-(CH_2)_v-CH=CH-(CH_2)_t-$ or $-(CH_2)_v-C\equiv C-(CH_2)_t-$, n, p, u, v and t independently of one another are each 1, 2 or 3, m is an integer from 2 to 10, and Az is 1,2,4-triazol-1-yl, pyrazol-1-yl or imidazol-1-yl, and their salts and metal complexes can be used successfully as bioregulators, i.e. agents for influencing plant growth, in the widest sense.

The action can extend to modification of the form of growth of the plants, alteration of substances present in the plants, and destruction of undesirable plants.

In formula (I), R and $R^1$ independently of one another are each, for example, halogen (fluorine, chlorine or bromine), nitro, cyano, alkyl or alkylsulfonyl, each of 1 to 4 carbon atoms, alkoxy or alkylthio, each of 1 or 2 carbon atoms, haloalkyl of 1 to 4, in particular 1 or 2, carbon atoms, and 1 to 5 halogen atoms, in particular 1 to 3 identical or different halogen atoms, preferred halogen atoms being fluorine and chlorine. Haloalkyl is particularly preferably trifluoromethyl.

R and $R^1$ independently of one another can furthermore be phenoxy or phenyl which is unsubstituted or, preferably, monosubstituted or polysubstituted (disubstituted or trisubstituted) by identical or different substituents, preferred substituents in each case being halogen, in particular fluorine, chlorine or bromine, cyano, nitro and haloalkyl of 1 or 2 carbon atoms and not more than 3 identical or different halogen atoms, preferred halogen atoms being fluorine and chlorine, and an example of haloalkyl being trifluoromethyl.

In formula (I), $R^2$ is preferably straight-chain or branched alkyl of 1 to 5 carbon atoms, e.g. methyl, ethyl, n-propyl, isopropyl, sec.-butyl or neopentyl. $R^2$ may furthermore be aralkyl where alkyl is of 1 to 4 carbon atoms, unsubstituted phenyl being the preferred aryl. Examples of aralkyl are thus benzyl, phenethyl, phenylpropyl and phenylbutyl. $R^2$ can also be allyl which is unsubstituted or substituted by 1, 2 or 3 chlorine atoms, or can be propargyl. Examples of allyl radicals are allyl, 2,3-dichloroallyl and 2,3,3-trichloroallyl.

In formula (I), $R^3$ is a divalent radical of the formula $-(CH_2)_m-$, for example $-CH_2CH_2-$, $-(CH_2)_3-$, $-(CH_2)_4-$, $-(CH_2)_5-$, $-(CH_2)_6-$, $-(CH_2)_7-$ or $-(CH_2)_8-$.

$R^3$ can furthermore be a divalent radical containing one, two or three oxygen atoms, of the formula $-(CH_2CH_2O)_uCH_2CH_2-$, for example $-CH_2CH_2OCH_2CH_2-$, $-CH_2CH_2OCH_2CH_2OCH_2CH_2-$ or $-(CH_2CH_2O)_3CH_2CH_2-$.

Finally, $R^3$ can be a divalent radical which contains a double or triple bond and is of the formula $-(CH_2)_v-CH=CH-(CH_2)_t$ or $-(CH_2)_v-C\equiv C-(CH_2)_t-$.

Examples are $-CH_2-CH=CH-CH_2-$, $-(CH_2)_2-CH=CH-(CH_2)_2-$, $-(CH_2)_3-CH=CH-(CH_2)_3-$, $-CH_2-CH=CH-CH_2-$, $-(CH_2)_2-C\equiv C-(CH_2)_2-$ and $-(CH_2)_3-C\equiv C-(CH_2)_3-$.

m is an integer from 2 to 10, preferably from 2 to 8.

If the agents are intended for use as growth regulators in the narrower sense, R, $R^1$, $R^2$, $R^3$, m, n, p, u and Az preferably have the following meanings:

R and $R^1$ independently of another are each F, Cl, Br, $C_1$-$C_5$-alkyl, methoxy, ethoxy, methylthio, ethylthio, $C_1$-$C_3$-haloalkyl containing not more than 4 fluorine or chlorine atoms, or unsubstituted or substituted phenyl or phenoxy, $R^2$ is hydrogen, $R^3$ is $-(CH_2)_m-$, $-(CH_2CH_2O)_u-CH_2CH_2-$, $-CH_2-CH=CH-CH_2-$ or $-CH_2-C\equiv C-CH_2-$, n, p and u are each 1, 2 or 3, m is from 2 to 8, and Az is 1,2,4-triazol-1-yl, pyrazol-1-yl or imidazol-1-yl; salts of the compounds can also be used.

Herbicidal agents are obtained in particular when $R^3$ is a divalent radical $-(CH_2)_m-$, where m is 2, 3 or 4.

Examples of salts of the azolylacetophenone oxime ethers of the formula (I) are the hydrochlorides, hydrobromides, sulfates, phosphates and p-toluenesulfonates.

A metal complex is, for example, an adduct of one equivalent of a zinc or copper salt, e.g. $CuCl_2$ or $ZnCl_2$, with two equivalents of a compound (I).

PREPARATION EXAMPLE 2,4-Dichloro-ω-[1,2,4-triazol-1-yl]-acetophenoneoxime O-[2-(4-chlorophenoxy)ethyl] ether, E and Z isomers 23 g (0.085 mole) of 2,4-dichloro-ω-[1,2,4-triazol-1-yl]-acetophenone oxime, 20 g of 2-[4-chlorophenoxy]-bromoethane, 7.1 g of powdered KOH and 5.8 g of triethylbenzylammonium chloride in 100 ml of toluene are stirred vigorously at 80°–100° C. for 1 hour. The mixture is evaporated down, the residue is taken up in 250 ml of dichloromethane, the solution is washed with three times 100 ml of water, and the organic phase is dried with sodium sulfate and evaporated down. Chromatography over silica gel, using dichloromethane as eluant, gives 6 g of the Z isomer (active ingredient No. 23) and 4 g of the E isomer of 2,4-dichloro-ω-[1,2,4-triazol-1-yl]-acetophenone oxime O-[2-(4-chlorophenoxy)-ethyl] ether (active ingredient No. 24). The Z isomer is the first to be eluted.

The compounds listed in the Table below can be prepared in a similar manner. The configuration in which the oxime oxygen and the C aromatic ring are on the same side of the oxime double bond is designated E, while the corresponding, other isomer is designated Z.

Tri=1,2,4-triazol-1-yl, Pyr=pyrazol-1-yl, Im-=imidazolyl, Ts=tosyl, Bu=butyl and Me=methyl.

Those compounds of the formula I which are shown in the Table below and for which melting points (mp.) or characteristics bands are given were prepared in a similar manner. Their structures were confirmed by elemental analysis. The compounds for which no physicochemical data are given can be obtained in the manner described for the compounds actually prepared; because of their similar constitution, they are expected to have actions similar to those of the compounds investigated in detail.

TABLE A

Compounds of the formula I with $R^3 = -(CH_2)_m-$:

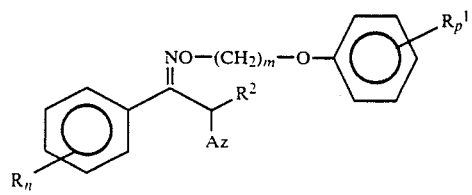

| No. | $R_n$ | $R_p^1$ | $R^2$ | Az | Configuration | m | M.p. [°C.] |
|---|---|---|---|---|---|---|---|
| 1 | H | H | H | Tri | E/Z mixture | 2 | |
| 2 | H | H | H | Tri | E/Z mixture | 4 | oil |
| 3 | H | H | H | Tri | E/Z mixture | 6 | |
| 4 | H | H | H | Tri | E/Z mixture | 8 | |
| 5 | 4-Cl | H | H | Tri | E/Z mixture | 2 | 96–98 |
| 6 | 4-Br | H | H | Tri | E/Z mixture | 2 | 89–90 |
| 7 | 4-OMe | H | H | Tri | E/Z mixture | 2 | |
| 8 | 4-CN | H | H | Tri | E/Z mixture | 2 | |
| 9 | 4-CF$_3$ | H | H | Tri | E/Z mixture | 2 | |
| 10 | 4-NO$_2$ | H | H | Tri | E/Z mixture | 2 | |
| 11 | 4-OC$_6$H$_5$ | H | H | Tri | E/Z mixture | 2 | |
| 12 | 2,4-Cl$_2$ | H | H | Tri.HNO$_3$ | E/Z mixture | 2 | 96 |
| 13 | 2,4-Cl$_2$ | H | H | Tri | Z | 3 | oil |
| 14 | 2,4-Cl$_2$ | H | H | Tri | E | 3 | oil |
| 15 | 2,4-Cl$_2$ | H | H | Tri | Z | 4 | oil |
| 16 | 2,4-Cl$_2$ | H | H | Tri | E | 4 | oil |
| 17 | 2,4-Cl$_2$ | H | H | Tri | Z | 5 | oil |
| 18 | 2,4-Cl$_2$ | H | H | Tri | E | 5 | oil |
| 19 | 2,4-Cl$_2$ | H | H | Tri | Z | 6 | oil |
| 20 | 2,4-Cl$_2$ | H | H | Tri | E | 6 | oil |
| 21 | 2,4-Cl$_2$ | H | H | Tri | E | 8 | |
| 22 | 2,4-Cl$_2$ | H | H | Tri | E | 8 | |
| 23 | 2,4-Cl$_2$ | 4-Cl | H | Tri | Z | 2 | 87–91 |
| 24 | 2,4-Cl$_2$ | 4-Cl | H | Tri | E | 2 | 58–61 |
| 25 | 2,4-Cl$_2$ | 4-Cl | H | Tri.HNO$_3$ | E/Z mixture | 2 | |
| 26 | 2,4-Cl$_2$ | 4-Cl | H | Tri.HNO$_3$ | E/Z mixture | 2 | |
| 27 | 2,4-Cl$_2$ | 4-Cl | H | Tri.H$_2$SO$_4$ | E/Z mixture | 2 | |
| 28 | 2,4-Cl$_2$ | 4-Cl | H | Tri.H$_3$PO$_4$ | E/Z mixture | 2 | |
| 29 | 2,4-Cl$_2$ | 4-Cl | H | Tri.TsOH | E/Z mixture | 2 | |
| 30 | 2,4-Cl$_2$ | 4-Cl | H | Tri.½CuCl$_2$ | E/Z mixture | 2 | |
| 31 | 2,4-Cl$_2$ | 4-Cl | H | Tri.½ZnCl$_2$ | E/Z mixture | 2 | |
| 32 | 2,4-Cl$_2$ | 4-Cl | CH$_3$ | Tri | E/Z mixture | 2 | |
| 33 | 2,4-Cl$_2$ | 4-Cl | n-Bu | Tri | E/Z mixture | 2 | |
| 34 | 2,4-Cl$_2$ | 4-Cl | CH$_2$C$_6$H$_5$ | Tri | E/Z mixture | 2 | |
| 35 | 2,4-Cl$_2$ | 4-Cl | CH$_2$C(CH$_3$)$_3$ | Tri | E/Z mixture | 2 | |
| 36 | 2,4-Cl$_2$ | 4-Cl | H | Tri | Z | 3 | oil |
| 37 | 2,4-Cl$_2$ | 4-Cl | H | Tri | E | 3 | oil |
| 38 | 2,4-Cl$_2$ | 4-Cl | H | Tri | Z | 4 | 65–71 |
| 39 | 2,4-Cl$_2$ | 4-Cl | H | Tri | E | 4 | oil |
| 40 | 2,4-Cl$_2$ | 4-Cl | H | Tri | Z | 5 | oil |
| 41 | 2,4-Cl$_2$ | 4-Cl | H | Tri | E | 5 | 59–62 |
| 42 | 2,4-Cl$_2$ | 2,4-Cl$_2$ | H | Tri | Z | 2 | 95–100 |
| 43 | 2,4-Cl$_2$ | 2,4-Cl$_2$ | H | Tri | E | 2 | oil |
| 44 | 2,4-Cl$_2$ | 2,4-Cl$_2$ | CH$_3$ | Tri | E/Z mixture | 2 | |
| 45 | 2,4-Cl$_2$ | 2,4-Cl$_2$ | n-Bu | Tri | E/Z mixture | 2 | |
| 46 | 2,4-Cl$_2$ | 2,4-Cl$_2$ | CH$_2$—C$_6$H$_5$ | Tri | E/Z mixture | 2 | |
| 47 | 2,4-Cl$_2$ | 2,4-Cl$_2$ | CH$_2$—C(CH$_3$) | Tri | E/Z mixture | 2 | |
| 48 | 2,4-Cl$_2$ | 2,4-Cl$_2$ | H | Tri.HNO$_3$ | E/Z mixture | 2 | 132 (decomposition) |
| 49 | 2,4-Cl$_2$ | 2,4,6-Cl$_3$ | H | Tri.HCl | E/Z mixture | 2 | |
| 50 | 2,4-Cl$_2$ | 2,4,6-Cl$_3$ | H | Tri.½ZnCl$_2$ | E/Z mixture | 2 | |
| 51 | 2,4-Cl$_2$ | 2,4,6-Cl$_3$ | H | Tri.½CuCl$_2$ | E/Z mixture | 2 | |
| 52 | 2,4-Cl$_2$ | 4-F | H | Tri | Z | 2 | 66–70 |
| 53 | 2,4-Cl$_2$ | 4-F | H | Tri | E | 2 | 73–77 |
| 54 | 2,4-Cl$_2$ | 4-CN | H | Tri | Z | 2 | 96–100 |
| 55 | 2,4-Cl$_2$ | 4-CN | H | Tri | E | 2 | |
| 56 | 2,4-Cl$_2$ | 4-tert.-Bu | H | Tri.HNO$_3$ | E/Z mixture | 2 | 117 |
| 57 | 2,4-Cl$_2$ | 4-OMe | H | Tri | Z | 2 | oil |
| 58 | 2,4-Cl$_2$ | 4-OMe | H | Tri | E | 2 | |
| 59 | 2,4-Cl$_2$ | 4-SMe | H | Tri | E/Z mixture | 2 | |
| 60 | 2,4-Cl$_2$ | 4-Br | H | Tri | E/Z mixture | 2 | |
| 61 | 2,4-Cl$_2$ | 4-NO$_2$ | H | Tri | E/Z mixture | 2 | |
| 62 | 2,4-Cl$_2$ | 3-Cl | H | Tri | Z | 2 | oil |

TABLE A-continued

Compounds of the formula I with $R^3 = -(CH_2)_m-$:

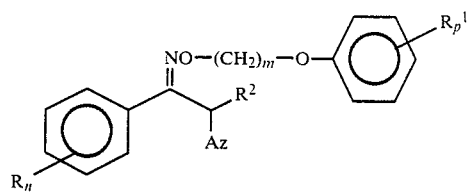

| No. | $R_n$ | $R_p^1$ | $R^2$ | Az | Configuration | m | M.p. [°C.] |
|---|---|---|---|---|---|---|---|
| 63 | 2,4-Cl$_2$ | 3-Cl | H | Tri | E | 2 | 73–77 |
| 64 | 2,4-Cl$_2$ | 3-CF$_3$ | H | Tri | Z | 2 | oil |
| 65 | 2,4-Cl$_2$ | 3-CF$_3$ | H | Tri | E | 2 | 66–69 |
| 66 | 2,4-Cl$_2$ | 4-Cl | CH$_2$HC=CH$_2$ | Tri | E/Z mixture | 2 | |
| 67 | 2,4-Cl$_2$ | 4-Cl | CH$_2$CCl=CCl$_2$ | Tri | E/Z mixture | 2 | |
| 68 | 2,4-Cl$_2$ | 4-Cl | propargyl | Tri | E/Z mixture | 2 | |
| 69 | 2,4-Cl$_2$-3-CH$_3$ | 4-Cl | H | Tri | E/Z mixture | 2 | oil |
| 70 | 2,5-Cl$_2$ | 4-Cl | H | Tri | Z | 2 | oil |
| 71 | 2,5-Cl$_2$ | H | H | Tri | E | 2 | 82–86 |
| 72 | 2,4-Cl$_2$ | H | H | Pyr | E/Z mixture | 2 | |
| 73 | 2,4-Cl$_2$ | H | H | Pyr | E/Z mixture | 3 | |
| 74 | 2,4-Cl$_2$ | H | H | Pyr | E/Z mixture | 4 | |
| 75 | 2,4-Cl$_2$ | H | H | Pyr | E/Z mixture | 5 | |
| 76 | 2,4-Cl$_2$ | 4-Cl | H | Pyr | E/Z mixture | 2 | |
| 77 | 2,4-Cl$_2$ | 4-F | H | Pyr | E/Z mixture | 2 | |
| 78 | 2,4-Cl$_2$ | 4-CN | H | Pyr | E/Z mixture | 2 | |
| 79 | 2,4-Cl$_2$ | 4-OMe | H | Pyr | E/Z mixture | 2 | |
| 80 | 2,4-Cl$_2$ | 4-Cl | CH$_3$ | Pyr | E/Z mixture | 2 | |
| 114 | 2,4-Cl$_2$ | 2,4,6-Cl$_3$ | H | Tri | Z isomer | 2 | 76–85 |
| 127 | 4-Cl | 2,4,6-Cl$_3$ | H | Tri | Z isomer | 2 | 114–116 |
| 128 | H | 4-Cl | H | Tri | Z isomer | 2 | 79–83 |
| 129 | H | 4-Cl | H | Tri | Z isomer | 3 | 59–64 |
| 130 | H | 4-Cl | H | Tri | Z isomer | 4 | 59–62 |
| 131 | H | 3-Cl | H | Tri | Z isomer | 2 | 73–75 |
| 132 | H | 3-CH$_3$ | H | Tri | Z isomer | 2 | 54–56 |
| 133 | H | H | H | Tri.½CuCl$_2$ | E/Z mixture | 4 | wax-like |
| 134 | H | H | H | Tri.HCl | E/Z mixture | 4 | wax-like |
| 135 | H | H | H | Tri | E/Z mixture | 4 | oil |
| 136 | H | 4-Cl | H | Tri.½CuCl$_2$ | E/Z mixture | 4 | wax-like |
| 137 | H | 4-Cl | H | Tri.HCl | E/Z mixture | 4 | 108–115 |
| 138 | H | 4-Cl | H | Tri | E/Z mixture | 4 | oil |
| 139 | H | 4-Cl | H | Tri.½CuCl$_2$ | E/Z mixture | 2 | wax-like |
| 140 | H | 4-Cl | H | Tri.HCl | E/Z mixture | 2 | 138–142 |
| 141 | H | 4-Cl | H | Tri | E/Z mixture | 2 | oil |
| 142 | H | 3-Cl | H | Tri | E/Z mixture | 2 | oil |
| 143 | H | 3-Cl | H | Tri.HCl | E/Z mixture | 2 | wax-like |
| 144 | H | 3-Cl | H | Tri.½CuCl$_2$ | E/Z mixture | 2 | wax-like |
| 145 | H | 3-CH$_3$ | H | Tri | E/Z mixture | 2 | oil |
| 146 | H | 3-CH$_3$ | H | Tri.HCl | E/Z mixture | 2 | wax-like |
| 147 | H | 3-CH$_3$ | H | Tri.½CuCl$_2$ | E/Z mixture | 2 | wax-like |
| 148 | 4-CH$_3$ | 4-Cl | H | Tri | Z isomer | 2 | 110–112 |
| 149 | 4-CH$_3$ | 4-Cl | H | Tri.HCl | Z isomer | 2 | 164–167 |
| 150 | 4-CH$_3$ | 3-Cl | H | Tri | Z isomer | 2 | 86–91 |
| 151 | 4-CH$_3$ | 3-Cl | H | Tri.HCl | Z isomer | 2 | oil |
| 152 | 4-CH$_3$ | 3-CH$_3$ | H | Tri | Z isomer | 2 | 66–71 |
| 153 | 4-CH$_3$ | 3-CH$_3$ | H | Tri.HCl | Z isomer | 2 | 125–128 |
| 154 | 4-CH$_3$ | 4-Cl | H | Tri | Z isomer | 3 | 70–72 |
| 155 | 4-CH$_3$ | 4-Cl | H | Tri.HCl | Z isomer | 3 | 160–163 |
| 156 | 4-CH$_3$ | H | H | Tri | Z isomer | 4 | 58–61 |
| 157 | 4-CH$_3$ | H | H | Tri.HCl | Z isomer | 4 | 120–124 |
| 158 | 4-CH$_3$ | 4-Cl | H | Tri | Z isomer | 4 | 75–76 |
| 159 | 4-CH$_3$ | 4-Cl | H | Tri.HCl | Z isomer | 4 | 123–125 |
| 160 | 4-Cl | 4-Cl | H | Tri | Z isomer | 2 | 133–135 |
| 161 | 4-Cl | 4-Cl | H | Tri.HCl | Z isomer | 2 | 174–178 |
| 162 | 4-Cl | 4-Cl | H | Tri | Z isomer | 4 | 75–81 |
| 163 | 4-Cl | 4-Cl | H | Tri.HCl | Z isomer | 4 | 128–130 |
| 164 | 4-Cl | H | H | Tri | Z isomer | 4 | 51–56 |
| 165 | 4-Cl | H | H | Tri.HCl | Z isomer | 4 | 136 |
| 166 | 4-Cl | 3-Cl | H | Tri | Z isomer | 2 | 89–94 |
| 167 | 4-Cl | 3-Cl | H | Tri.HCl | Z isomer | 2 | 141–145 |
| 168 | 4-Cl | 3-CH$_3$ | H | Tri | Z isomer | 2 | 103–105 |
| 169 | 4-Cl | 3-CH$_3$ | H | Tri.HCl | Z isomer | 2 | 107–108 |
| 179 | 4-Cl | 3-CF$_3$ | H | Tri | | 2 | 89–93 |
| 180 | 4-Cl | 3,5-Cl$_2$ | H | Tri | | 2 | 88–94 |
| 181 | 4-CH$_3$ | 3,5-Cl$_2$ | H | Tri | | 2 | 70–74 |
| 182 | 4-Cl | 3-Cl | H | Tri | | 3 | 67–69 |
| 183 | 4-CH$_3$ | 3-Cl | H | Tri | | 2 | 54–57 |
| 184 | 4-Cl | 3-Cl | H | Im | | 2 | 119–123 |
| 185 | 4-Cl | 3-Cl | H | Pyr | | 2 | 73–78 |
| 186 | H | 3-Cl | H | Im | | 2 | |

TABLE A-continued

Compounds of the formula I with $R^3 = -(CH_2)_m-$:

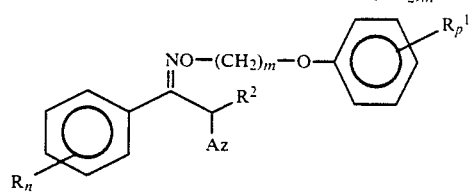

| No. | $R_n$ | $R_p^1$ | $R^2$ | Az | Configuration | m | M.p. [°C.] |
|---|---|---|---|---|---|---|---|
| 187 | H | 3-Cl | H | Pyr | | 2 | oil |
| 188 | 4-Cl | 3,4-Cl$_2$ | H | Tri | Z isomer | 2 | 83 |
| 189 | 4-Cl | 2,3-Cl$_2$ | H | Tri | Z isomer | 2 | 103–106 |
| 190 | 4-Cl | 3-OCH$_3$ | H | Tri | Z isomer | 2 | 99 |
| 191 | 3,4-Cl$_2$ | 3-Cl | H | Tri | Z isomer | 2 | 84 |
| 192 | 4-F | 3-Cl | H | Tri | Z isomer | 2 | 71–74 |
| 193 | 3,4-Cl$_2$ | 3-CH$_3$ | H | Tri | Z isomer | 2 | 73–75 |
| 194 | 4-F | 3-CH$_3$ | H | Tri | Z isomer | 2 | 63–65 |
| 195 | 4-Cl | 3-NO$_2$ | H | Tri | Z isomer | 2 | 135–137 |
| 196 | 4-C$_6$H$_5$ | 3-Cl | H | Tri | Z/E mixture | 2 | 60–63 |
| 197 | 4-C$_6$H$_5$ | 3-CH$_3$ | H | Tri | Z/E mixture | 2 | wax-like |
| 198 | 4-Cl | 2,4,5-Cl$_3$ | H | Tri | Z/E mixture | 2 | 89 |
| 199 | 4-Cl | 2,5-Cl$_2$ | H | Tri | Z/E mixture | 2 | 124–126 |
| 200 | 4-OCH$_3$ | 3-CF$_3$ | H | Tri | Z/E mixture | 2 | 64–67 |
| 201 | 4-C$_6$H$_5$ | 3-CF$_3$ | H | Tri | Z/E mixture | 2 | 87–90 |
| 202 | 4-F | 3-CF$_3$ | H | Tri | Z/E mixture | 2 | 70–74 |
| 203 | 3,4-Cl$_2$ | 3-CF$_3$ | H | Tri | Z/E mixture | 2 | 90–94 |
| 204 | 4-OCH$_3$ | 3-Cl | H | Tri | Z/E mixture | 2 | 48–50 |
| 205 | 4-OCH$_3$ | 3-CH$_3$ | H | Tri | Z/E mixture | 2 | oil |
| 206 | H | 3-CH$_3$ | H | Tri | Z/E mixture | 2 | |
| 207 | 4-(CH$_3$)$_2$CH— | 3-Cl | H | Tri | Z/E mixture | 2 | |
| 208 | 4-(CH$_3$)$_2$CH— | 3-CH$_3$ | H | Tri | Z/E mixture | 2 | |
| 209 | 4-(CH$_3$)$_2$CH— | 3,4-Cl$_2$ | H | Tri | Z/E mixture | 2 | |
| 210 | 4-(CH$_3$)$_2$CH— | 2,3-Cl$_2$ | H | Tri | Z/E mixture | 2 | |
| 211 | 4-(CH$_3$)$_2$C— | 3-CH$_3$ | H | Tri | Z/E mixture | 2 | |
| 212 | 4-(CH$_3$)$_2$C— | 3-Cl | H | Tri | Z/E mixture | 2 | |
| 213 | 4-(CH$_3$)$_3$C— | 3,4-Cl$_2$ | H | Tri | Z/E mixture | 2 | |
| 214 | 4-(CH$_3$)$_3$C— | 2,3-Cl$_2$ | H | Tri | Z/E mixture | 2 | |
| 215 | 4-cycl.-C$_6$H$_{11}$ | 3-CH$_3$ | H | Tri | Z/E mixture | 2 | |
| 216 | 4-cycl.-C$_6$H$_{11}$ | 3-Cl | H | Tri | Z/E mixture | 2 | |
| 217 | 4-cycl.-C$_6$H$_{11}$ | 3,4-Cl$_2$ | H | Tri | Z/E mixture | 2 | |
| 218 | 4-cycl.-C$_6$H$_{11}$ | 2,3-Cl$_2$ | H | Tri | Z/E mixture | 2 | |
| 219 | 4-C$_6$H$_5$ | 2,3-Cl$_2$ | H | Tri | Z/E mixture | 2 | |
| 220 | 4-C$_6$H$_5$ | 2,3-Cl$_2$ | H | Tri | Z/E mixture | 2 | |
| 221 | 4-OCH$_3$ | 2,3-Cl$_2$ | H | Tri | Z/E mixture | 2 | |
| 222 | 4-OCH$_3$ | 3,4-Cl$_2$ | H | Tri | Z/E mixture | 2 | |
| 223 | 4-OC$_6$H$_5$ | 3-Cl | H | Tri | Z/E mixture | 2 | |
| 224 | 4-OC$_6$H$_5$ | 3-OCH$_3$ | H | Tri | Z/E mixture | 2 | |
| 225 | 4-OC$_6$H$_5$ | 2,3-Cl$_2$ | H | Tri | Z/E mixture | 2 | |
| 226 | 4-OC$_6$H$_5$ | 3,4-Cl$_2$ | H | Tri | Z/E mixture | 2 | |
| 237 | 4-NO$_2$ | 3-Cl | H | Tri | Z/E mixture | 2 | |
| 238 | 4-NO$_2$ | 3-CH$_3$ | H | Tri | Z/E mixture | 2 | |
| 239 | 4-NO$_2$ | 3,4-Cl$_2$ | H | Tri | Z/E mixture | 2 | |
| 240 | 4-NO$_2$ | 2,3-Cl$_2$ | H | Tri | Z/E mixture | 2 | |
| 241 | 2-Cl | 3-Cl | H | Tri | Z/E mixture | 2 | |
| 242 | 2-Cl | 3-CH$_3$ | H | Tri | Z/E mixture | 2 | |
| 243 | 2-Cl | 2,3-Cl$_2$ | H | Tri | Z/E mixture | 2 | |
| 244 | 2-Cl | 3,4-Cl$_2$ | H | Tri | Z/E mixture | 2 | |
| 245 | 3,5-Cl$_2$ | 3-Cl | H | Tri | Z/E mixture | 2 | |
| 246 | 3,5-Cl$_2$ | 3-CH$_3$ | H | Tri | Z/E mixture | 2 | |
| 247 | 4-Br | 3-Cl | H | Tri | Z/E mixture | 2 | |
| 248 | 4-Br | 3-CH$_3$ | H | Tri | Z/E mixture | 2 | |
| 249 | H | 3-Cl | —CH$_3$ | Tri | Z/E mixture | 2 | |
| 250 | H | 3-CH$_3$ | —CH$_3$ | Tri | Z/E mixture | 2 | |
| 251 | H | 3-Cl | —CH$_2$CH$_3$ | Tri | Z/E mixture | 2 | |
| 252 | H | 3-CH$_3$ | —CH$_2$CH$_3$ | Tri | Z/E mixture | 2 | |
| 253 | H | 3-Cl | —CH$_2$CH$_2$CH$_3$ | Tri | Z/E mixture | 2 | |
| 254 | H | 3-CH$_3$ | —CH$_2$CH$_2$CH$_3$ | Tri | Z/E mixture | 2 | |
| 255 | 4-F | 3-F | H | Tri | Z/E mixture | 2 | |
| 256 | H | 2-F | H | Tri | Z | 2 | |
| 257 | H | 2-F | H | Tri | E | 2 | |
| 258 | H | 2-Cl | H | Tri | Z | 2 | |
| 259 | H | 2-Cl | H | Tri | E | 2 | |
| 260 | 4-CH$_3$ | 2-F | H | Tri | Z | 2 | |
| 261 | 4-CH$_3$ | 2-F | H | Tri | E | 2 | |
| 262 | 4-CH$_3$ | 2-Cl | H | Tri | Z | 2 | |
| 263 | 4-CH$_3$ | 2-Cl | H | Tri | E | 2 | |
| 264 | 4-cycl.C$_6$H$_{11}$ | 2-F | H | Tri | Z | 2 | |
| 265 | 4-cycl.C$_6$H$_{11}$ | 2-F | H | Tri | E | 2 | 77–80 |
| 266 | 4-cycl.C$_6$H$_{11}$ | 2-Cl | H | Tri | Z | 2 | |

TABLE A-continued

Compounds of the formula I with $R^3 = -(CH_2)_m-$:

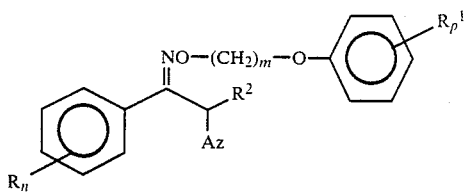

| No. | $R_n$ | $R_p{}^1$ | $R^2$ | Az | Configuration | m | M.p. [°C.] |
|---|---|---|---|---|---|---|---|
| 267 | 4-cycl.$C_6H_{11}$ | 2-Cl | H | Tri | E | 2 | wax-like |
| 268 | 4-$C_6H_5$ | 2-F | H | Tri | Z | 2 | 111 |
| 269 | 4-$C_6H_5$ | 2-F | H | Tri | E | 2 | |
| 270 | 4-$C_6H_5$ | 2-Cl | H | Tri | Z | 2 | 108 |
| 271 | 4-$C_6H_5$ | 2-Cl | H | Tri | E | 2 | |
| 272 | 4-Cl | 2-F | H | Tri | Z | 2 | |
| 273 | 4-Cl | 2-F | H | Tri | E | 2 | |
| 274 | 4-Cl | 2-Cl | H | Tri | Z | 2 | |
| 275 | 4-Cl | 2-Cl | H | Tri | E | 2 | |
| 276 | 4-F | 2-Cl | H | Tri | E/Z mixture | 2 | 74–77 |
| 277 | 4-F | 2-Cl | H | Tri | Z | 2 | 81 |
| 278 | 4-F | 2-Cl | H | Tri | E | 2 | |
| 279 | 4-F | 2-F | H | Tri | Z | 2 | 86 |
| 280 | 4-F | 2-F | H | Tri | E | 2 | |
| 281 | 4-$OCH_3$ | 2-F | H | Tri | Z | 2 | 79–81 |
| 282 | 4-$OCH_3$ | 2-F | H | Tri | E | 2 | |
| 283 | 4-$OCH_3$ | 2-Cl | H | Tri | Z | 2 | 71 |
| 284 | 4-$OCH_3$ | 2-Cl | H | Tri | E | 2 | |
| 285 | 4-CN | 2-F | H | Tri | Z | 2 | |
| 286 | 4-CN | 2-F | H | Tri | E | 2 | |
| 287 | H | 2-CN | H | Tri | Z | 2 | |
| 288 | H | 2-CN | H | Tri | E | 2 | |
| 289 | 4-$CH_3$ | 2-CN | H | Tri | Z | 2 | |
| 290 | 4-$CH_3$ | 2-CN | H | Tri | E | 2 | |
| 291 | 4-Cl | 2-CN | H | Tri | Z | 2 | |
| 292 | 4-Cl | 2-CN | H | Tri | E | 2 | |
| 293 | 4-F | 2-CN | H | Tri | Z | 2 | |
| 294 | 4-F | 2-CN | H | Tri | E | 2 | |
| 295 | H | 2-$CH_3$ | H | Tri | Z | 2 | |
| 296 | H | 2-$CH_3$ | H | Tri | E | 2 | |
| 297 | 4-$CH_3$ | 2-$CH_3$ | H | Tri | Z | 2 | |
| 298 | 4-$CH_3$ | 2-$CH_3$ | H | Tri | E | 2 | |
| 299 | 4-Cl | 2-$CH_3$ | H | Tri | Z | 2 | |
| 300 | 4-Cl | 2-$CH_3$ | H | Tri | E | 2 | |
| 301 | 4-F | 2-$CH_3$ | H | Tri | Z | 2 | |
| 302 | 4-F | 2-$CH_3$ | H | Tri | E | 2 | |
| 303 | H | 2-$OCH_3$ | H | Tri | Z | 2 | |
| 304 | H | 2-$OCH_3$ | H | Tri | E | 2 | |
| 305 | 2-$CH_3$ | 2-$OCH_3$ | H | Tri | Z | 2 | |
| 306 | 2-$CH_3$ | 2-$OCH_3$ | H | Tri | E | 2 | |
| 307 | 2-Cl | 2-$OCH_3$ | H | Tri | Z | 2 | |
| 308 | 2-Cl | 2-$OCH_3$ | H | Tri | E | 2 | |
| 309 | 2-F | 2-$OCH_3$ | H | Tri | Z | 2 | |
| 310 | 2-F | 2-$OCH_3$ | H | Tri | E | 2 | |
| 311 | 3-Cl | 2-Cl | H | Tri | Z | 2 | |
| 312 | 3-Cl | 2-F | H | Tri | Z | 2 | |
| 313 | 3-Br | 2-Cl | H | Tri | Z | 2 | |
| 314 | 3,4-$Cl_2$ | 2-Cl | H | Tri | Z | 2 | 98 |
| 315 | 3,4-$Cl_2$ | 2-F | H | Tri | Z | 2 | 103–105 |
| 316 | 3,5-$Cl_2$ | 2-F | H | Tri | Z | 2 | 117 |
| 317 | 3,5-$Cl_2$ | 2-Cl | H | Tri | Z | 2 | 108 |
| 318 | 2,5-$Cl_2$ | 2-F | H | Tri.$HNO_3$ | Z | 2 | 110 |
| 319 | 2,5-$Cl_2$ | 2-Cl | H | Tri | Z | 2 | wax-like |
| 320 | 2,4-$Cl_2$ | 2-F | H | Tri | Z | 2 | |
| 321 | 2,4-$Cl_2$ | 2-Cl | H | Tri | Z | 2 | |
| 322 | 2-Cl | 2-F | H | Tri | Z | 2 | |
| 323 | 2-Cl | 2-Cl | H | Tri | Z | 2 | |
| 324 | H | 2,6-$Cl_2$ | H | Tri | Z | 2 | |
| 325 | 4-$CH_3$ | 2,6-$Cl_2$ | H | Tri | Z | 2 | |
| 326 | 4-Cl | 2,6-$Cl_2$ | H | Tri | Z | 2 | |
| 327 | 4-F | 2,6-$Cl_2$ | H | Tri | Z | 2 | |
| 328 | 2,5-$Cl_2$ | 3-Cl | H | Tri | Z | 2 | oil |
| 329 | 3-Br | 3-Cl | H | Tri | Z | 2 | 100–103 |

TABLE B

Compounds of the formula I with $R^3 = -(CH_2CH_2O)_uCH_2CH_2-$

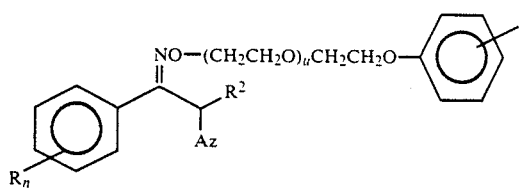

| No. | $R_n$ | $R_p^1$ | $R^2$ | Az | Configuration | m | M.p. [°C.] |
|---|---|---|---|---|---|---|---|
| 81 | 2,4-Cl$_2$ | H | H | Tri | E/Z mixture | 1 | |
| 82 | 2,4-Cl$_2$ | H | H | Tri | E/Z mixture | 2 | oil |
| 83 | 2,4-Cl$_2$ | H | H | Tri | E/Z mixture | 3 | |
| 84 | 2,4-Cl$_2$ | 4-Cl | H | Tri | E/Z mixture | 1 | |
| 85 | 2,4-Cl$_2$ | 4-Cl | H | Tri | E/Z mixture | 2 | oil |
| 86 | 2,4-Cl$_2$ | 4-Cl | H | Tri | E/Z mixture | 3 | |
| 87 | 2,4-Cl$_2$ | 2,4-Cl$_2$ | H | Tri | E/Z mixture | 1 | |
| 88 | 2,4-Cl$_2$ | 2,4-Cl$_2$ | H | Tri | E/Z mixture | 2 | oil |
| 89 | 2,4-Cl$_2$ | 2,4-Cl$_2$ | H | Tri | E/Z mixture | 3 | |
| 106 | 2,4-Cl$_2$ | 2-Cl | H | Tri | E/Z mixture | 2 | oil |
| 107 | 2,4-Cl$_2$ | 3-Cl | H | Tri | E/Z mixture | 2 | oil |
| 108 | 2,4-Cl$_2$ | 4-OCH$_3$ | H | Tri | Z isomer | 2 | oil |
| 109 | 2,4-Cl$_2$ | 2,4,6-Cl$_3$ | H | Tri | Z isomer | 2 | oil |

TABLE C

Compounds of the formula I with $R^3 = -(CH_2)_v-CH=CH-(CH_2)_t-$

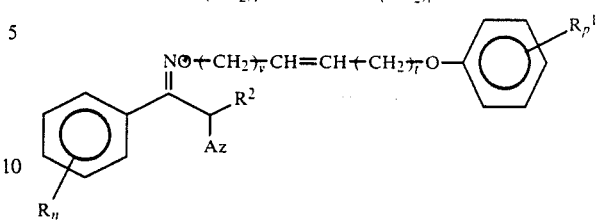

| No. | $R_n$ | $R_p^1$ | $R^2$ | Az | Configuration | v | t | M.p. [°C.] |
|---|---|---|---|---|---|---|---|---|
| 90 | 2,4-Cl$_2$ | 4 | H | Tri | E/Z mixture | 1 | 1 | oil |
| 91 | 2,4-Cl$_2$ | 4-Cl | H | Tri | E/Z mixture | 1 | 1 | oil |
| 92 | 2,4-Cl$_2$ | 4-CH$_3$ | H | Tri | E/Z mixture | 1 | 1 | |
| 93 | 2,4-Cl$_2$ | 4-OCH$_3$ | H | Tri | E/Z mixture | 1 | 1 | |
| 94 | 2,4-Cl$_2$ | 2,4-Cl$_2$ | H | Tri | E/Z mixture | 1 | 1 | oil |
| 95 | 2,4-Cl$_2$ | 2,4,6-Cl$_3$ | H | Tri | E/Z mixture | 1 | 1 | oil |
| 96 | 2,4-Cl$_2$ | 4-Cl | H | Tri | E/Z mixture | 2 | 2 | |
| 97 | 2,4-Cl$_2$ | 4-Cl | H | Tri | E/Z mixture | 3 | 3 | |
| 115 | 2,4-Cl$_2$ | 2-Cl | H | Tri | E/Z mixture | 1 | 1 | 84 |

TABLE D

Compounds of the formula I with $R^3 = -(CH_2)_v-C\equiv C-(CH_2)_t-$

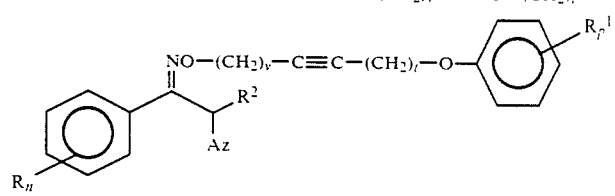

| No. | $R_n$ | $R_p^1$ | $R^2$ | Az | Configuration | v | t | M.p. [°C.] |
|---|---|---|---|---|---|---|---|---|
| 98 | 2,4-Cl$_2$ | H | H | Tri | E/Z mixture | 1 | 1 | oil |
| 99 | 2,4-Cl$_2$ | 4-Cl | H | Tri | E/Z mixture | 1 | 1 | oil |
| 100 | 2,4-Cl$_2$ | 4-CH$_3$ | H | Tri | E/Z mixture | 1 | 1 | oil |
| 101 | 2,4-Cl$_2$ | 4-OCH$_3$ | H | Tri | E/Z mixture | 1 | 1 | oil |
| 102 | 2,4-Cl$_2$ | 2,4-Cl$_2$ | H | Tri | E/Z mixture | 1 | 1 | oil |
| 103 | 2,4-Cl$_2$ | 3-CH$_3$ | H | Tri | E/Z mixture | 1 | 1 | oil |
| 104 | 2,4-Cl$_2$ | 4-Cl | H | Tri | E/Z mixture | 2 | 2 | |
| 105 | 2,4-Cl$_2$ | 4-Cl | H | Tri | E/Z mixture | 3 | 3 | |
| 172 | 2,4-Cl$_2$ | 4-F | H | Tri | Z isomer | 1 | 1 | oil |
| 173 | 2,4-Cl$_2$ | 3-Cl | H | Tri | Z isomer | 1 | 1 | oil |
| 174 | 4-Cl | H | H | Tri | Z isomer | 1 | 1 | 70–75 |
| 175 | 4-Cl | 4-Cl | H | Tri | Z isomer | 1 | 1 | 81–85 |
| 176 | 4-Cl | 4-F | H | Tri | Z isomer | 1 | 1 | 70–75 |
| 177 | 4-Cl | 3-Cl | H | Tri | Z isomer | 1 | 1 | 80–85 |
| 178 | 4-Cl | 4-OCH$_3$ | H | Tri | Z isomer | 1 | 1 | oil |

| No. | $R_n$ | $R_p^1$ | $R^2$ | Az | Configuration | m | M.p. |
|---|---|---|---|---|---|---|---|
| 110 | 2,4-Cl$_2$ | 2-Cl | H | Tri | E/Z mixture | 1 | wax-like |
| 111 | 2,4-Cl$_2$ | 4-OCH$_3$ | H | Tri | Z isomer | 1 | wax-like |
| 112 | 2,4-Cl$_2$ | 3-CH$_3$ | H | Tri | Z isomer | 1 | wax-like |
| 113 | 2,4-Cl$_2$ | 4-CH$_3$ | H | Tri | Z isomer | 1 | wax-like |
| 116 | 4-Cl | 2,4,6-Cl$_3$ | H | Tri | Z isomer | 1 | 69–71 |
| 117 | 4-Cl | 2-Cl | H | Tri | Z isomer | 1 | 63–65 |
| 118 | 4-Cl | 3-CH$_3$ | H | Tri | Z isomer | 1 | 66–68 |
| 119 | 4-Cl | 4-OCH$_3$ | H | Tri | Z isomer | 1 | 71 |
| 120 | 4-Cl | 4-CH$_3$ | H | Tri | Z isomer | 1 | 79 |
| 121 | 4-Cl | H | H | Tri | Z isomer | 2 | oil |
| 122 | 4-Cl | 4-Cl | H | Tri | Z isomer | 2 | 85–88 |
| 123 | 4-Cl | 2-Cl | H | Tri | Z isomer | 2 | oil |
| 124 | 4-Cl | 3-Cl | H | Tri | Z isomer | 2 | oil |
| 125 | 4-Cl | 2,4-Cl$_2$ | H | Tri | Z isomer | 2 | 48–53 |
| 126 | 4-Cl | 4-OCH$_3$ | H | Tri | Z isomer | 2 | oil |
| 170 | 4-CH$_3$ | 4-Cl | H | Tri | Z isomer | 2 | oil |
| 171 | H | 4-Cl | H | Tri | Z isomer | 2 | oil |

Characteristic NMR data ($^1$H-NMR):

| No. | δ in ppm, solvent CDCl$_3$ |
|---|---|
| 13 | 4.05 "t" 2H; 4.45 "t" 2H; 5.39 s 2H; 7.72 s 1H; 7.98 s 1H |
| 14 | 3.90 "t" 2H; 4.25 "t" 2H; 5.10 s 2H; 7.82 s 1H; 7.90 s 1H |
| 15 | 4.00 "t" 2H; 4.35 "t" 2H; 5.40 s 2H; 7.80 s 1H; 8.07 s 1H |
| 16 | 3.90 "t" 2H; 4.20 "t" 2H; 5.20 s 2H; 7.90 s 1H; 8.00 s 1H |
| 17 | 4.00 "t" 2H; 4.30 "t" 2H; 5.44 s 2H; 7.82 s 1H; 8.10 s 1H |
| 18 | 3.90 "t" 2H; 4.20 "t" 2H; 5.20 s 2H; 7.93 s 1H; 8.04 s 1H |
| 36 | 4.03 "t" 2H; 4.43 "t" 2H; 5.44 s 2H; 7.80 s 1H; 8.07 s 1H |
| 37 | 3.90 "t" 2H; 4.27 "t" 2H; 5.20 s 2H; 7.90 s 1H; 8.00 s 1H |
| 39 | 3.78 "t" 2H; 4.08 "t" 2H; 5.05 s 2H; 7.70 s 1H; 7.85 s 1H |
| 40 | 3.38 "t" 2H; 4.20 "t" 2H; 5.35 s 2H; 7.70 s 1H; |

-continued

| No. | Characteristic NMR data ($^1$H-NMR): δ in ppm. solvent CDCl$_3$ |
|---|---|
| | 7.98 s 1H |
| 43 | 4.22 "t" 2H; 4.48 "t" 2H; 5.23 s 2H; 7.98 s 1H; 8.03 s 1H |
| 57 | 4.25 "t" 2H; 4.60 "t" 2H; 5.47 s 2H; 7.80 s 1H; 8.17 s 1H |
| 62 | 4.27 "t" 2H; 4.60 "t" 2H; 5.48 s 2H; 7.80 s 1H; 8.15 s 1H |
| 64 | 4.43 "t" 2H; 4.63 "t" 2H; 5.45 s 2H; 7.80 s 1H; 8.13 s 1H |
| 69 | 2.41 3H; 4.22 "t" 2H; 4.58 "t" 2H; 5.41 s 2H; 7.78 s 1H; 8.11 s 1H |
| 70 | 4.22 "t" 2H; 4.59 "t" 2H; 5.42 s 2H; 7.81 s 1H; 8.14 s 1H |
| 98 | 4.78 s 4H; 5.22 2H; 7.93 s 1H; 8.03 s 1H |
| 100 | 2.28 3H; 4.70 m 3H; 5.20 s 2H; 7.90 s 1H; 8.00 s 1H |
| 101 | 3.72 s 3H; 4.70 s 2H; 4.87 s 2H; 5.44 s 2H; 7.80 s 1H; 8.11 s 1H |
| 102 | 4.70 m 4H; 5.20 s and 5.50 s 2H; 7.80 s and 7.94 s 1H; 8.01 s and 8.10 s 1H |
| 103 | 2.31 s 3H; 4.72 s 2H; 4.87 s 2H; 5.44 s 2H; 7.80 s 1H; 8.10 s 1H |
| 112 | 3.75 m 4H; 4.15 m 2H; 4.35 m 2H, 5.53 s 2H; 7.83 s 1H; 8.50 s 1H |
| 113 | 3.75 m 4H; 4.15 m 2H; 4.38 m 2H; 5.53 s 2H; 7.85 s 1H; 8.50 s 1H |
| 121 | 3.75 m 8H; 4.15 m 2H; 4.40 m 2H; 5.35 s 2H; 7.88 s 1H; 8.38 s 1H |
| 123 | 3.80 m 8H; 4.15 m 2H; 4.45 m 2H; 5.38 s 2H; 7.88 s 1H; 8.38 s 1H |
| 124 | 3.70 m 8H; 4.15 m 2H; 4.30 m 2H; 5.45 s 2H; 7.78 s 1H; 8.45 s 1H |
| 126 | 3.80 m 8H; 4.10 m 2H; 4.40 m 2H; 5.60 s 2H; 8.05 s 1H; 8.70 s 1H |
| 170 | 3.70 m 8H; 4.00 m 2H; 4.35 m 2H; 5.30 s 2H; 7.75 s 1H; 8.43 s 1H |
| 171 | 3.80 m 8H; 4.10 m 2H; 4.45 m 2H; 5.40 s 2H; 7.90 s 1H; 8.40 s 1H |
| 172 | 4.60 "t" 2H; 4.80 "t" 2H; 5.40 s 2H;. 7.70 s 1H; 7.98 s 1H |
| 173 | 4.65 "t" 2H; 4.85 "t" 2H; 5.40 s 2H;, 7.70 s 1H; 8.00 s 1H |
| 141 | 4.20 "t" 2H; 4.45 "t" 2H; 5.21 s 2H; 7.91 s 1H; 8.13 s 1H |
| 142 | 4.20 "t" 2H; 4.42 "t" 2H; 5.19 s 2H; 7.90 s 1H; 8.02 s 1H |
| 145 | 4.20 "t" 2H; 4.45 "t" 2H; 5.20 s 2H; 7.90 s 1H; 8.02 s 1H |
| 135 | 1.8 m 4H; 3.90 "t" 2H; 4.18 "t" 2H; 5.18 s 2H; 7.89 s 1H; 8.00 s 1H |
| 106 | 3.7 m 8H; 4.2 m 4H; 5.55 s 2H; 7.87 s 1H; 8.52 s 1 H |
| 107 | 3.7 m 8H; 4.2 m 4H; 5.57 s 2H; 7.85 s 1H; 8.50 s 1H |
| 108 | 3.7 m 8H; 4.0 m 2H;; 4.45 m 2H; 5.55 s 2H; 7.88 s 1H; 8.5 s 1H |
| 109 | 3.7 m 8H; 4.25 m 4H; 5.55 s 2H; 7.85 s 1H; 8.50 s 1H |
| 110 | 3.8 m 4H; 4.20 m 4H; 5.45 s 2H; 7.75 s 1H; 8.40 s 1H |
| 111 | 3.75 m 4H; 4.05 m 2H; 4.35 m 2H; 5.53 s 2H; 7.83 s 1H; 8.50 s 1H |
| 178 | 4.65 "t" 2H; 4.85 "t" 2H; 5.30 s 2H; 7.80 s 1H; 8.10 s 1H |
| 186 | 4.30 "t" 2H; 4.65 "t" 2H; 5.22 s 2H; 6.8-7.7 m; 12H |
| 187 | 4.20 m 2H; 4.55 m 2H; 5.35 s 2H; 6.08 t 1H; 6.6-7.8 m; 1H |
| 197 | 4.25 "t" 2H; 4.60 "t" 2H; 5.42 s 2H; 7.88 s 1H; 8.28 s 1H |
| 205 | 4.25 "t" 2H; 4.55 "t" 2H; 5.32 s 2H; 7.90 s 1H; 8.28 s 1H. | s = singlet
"t" = pseudo-triplet
m = multiplet

The novel compounds may influence virtually all development stages of a plant in different ways, and are therefore employed as growth regulators or herbicides.

USE EXAMPLES

I. To determine the growth-regulating properties of the candidate compounds, soil provided with sufficient nutrients was filled into plastic pots about 12.5 cm in diameter and summer rape plants were growth therein.

The compounds were sprayed onto the plants (post-emergence treatment). The growth-regulating action observed was confirmed at the end of the experiment by height measurements. The values obtained were compared with those for untreated plants.

The compounds used for comparison purposes were active ingredients A and B having the structural formulae given below.

Not only was growth height reduced—the leaves also took on a more intense color. The increased chlorophyll content is indicative of a higher rate of photosynthesis, making for bigger yields.

Comparative agents:

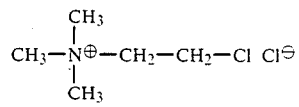

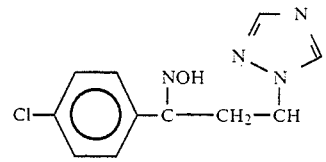

The results show that active ingredients 13, 15, 52, 57, 62, 64, 101, 103, 116, 117, 119, 121, 122 and 123, applied for example at a rate of 1.5 or 6 mg per vessel, reduced growth height to a greater extent (e.g., 68% or 57%) than active ingredients A and B (e.g., 94% and 83%).

II. In the same manner as described under I, summer wheat of the Kalibri variety (Table 1) and summer barley of the Aramir variety (Table 2) were treated post-emergence. The following results were obtained:

TABLE 1

| No. of chemical example | mg of active ingredient per vessel | Relative growth height |
|---|---|---|
| — | — | 100 |
| A | 1.5 | 99.2 |
| | 6 | 84.8 |
| B | 1.5 | 99.5 |
| | 6 | 94.0 |
| 131 | 1.5 | 73.2 |
| | 6 | 71.6 |
| 142 | 1.5 | 79.2 |
| | 6 | 73.2 |
| 255 | 1.5 | 77.4 |
| | 6 | 71.9 |
| 276 | 1.5 | 70.1 |
| | 6 | 70.1 |

TABLE 2

| No. of chemical example | mg of active ingredient per vessel | Relative growth height |
|---|---|---|
| — | — | 100 |
| A | 1.5 | 93.4 |
| | 6 | 93.4 |
| B | 1.5 | 95.3 |
| | 6 | 95.3 |
| 131 | 1.5 | 86.8 |
| | 6 | 77.2 |
| 142 | 1.5 | 92.9 |
| | 6 | 92.9 |
| 255 | 1.5 | 87.9 |
| | 6 | 84.3 |
| 276 | 1.5 | 84.3 |

TABLE 2-continued

| No. of chemical example | mg of active ingredient per vessel | Relative growth height |
|---|---|---|
| | 6 | 84.3 |

The herbicidal action of compounds of the formula I is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rates were 3.0 and 1.0 kg of active ingredient per hectare. After the agents had been applied, the vessels were lightly sprinkler-irrigated to induce germination an growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean and rice plants were grown in a peat-enriched substrate. For this treatment, either plants which had been sown directly in the pots and grown there were selected, or plants which had been grown from seedlings and were transplanted to the pots a few days before treatment. The application rate for postemergence treatment was for example 1.0 kg of active ingredient per hectare.

The pots were set up in the greenhouse—species from warmer areas at from 20° to 30° C., and species from moderate climates at 15° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus spp., Centaurea cyanus, Chenopodium album, Echinochloa, crus-galli, Galeopsis spp., Gaalium aparine, Glycine max., Ipomoea spp., Lamium amplexicaule, Lolium multiflorum, Lycopersicon lycopersicum, Mercurialis annua, Stellaria media, Triticum aestivum, Viola spp., and Zea mays.

At an application rate of 3.0 kg/ha, compounds nos. 131, 153, 166 and 192 had a considerable herbicidal action on broadleaved and grassy plants (postemergence application).

Compound no. 166, applied postemergence at a rate of 0.5 kg/ha, and compounds nos. 133, 142, 143, 150 and 167 at 1.0 kg/ha are suitable for selectively combatting unwanted plants in crops. Compounds nos. 166 and 204 combatted broadleaved weeds at a rate of 2.0 kg/ha.

TABLE 3

Selective control of broadleaved unwanted plants in wheat on postemergence application in the greenhouse

| Compound no. | kg/ha | Test plants and % damage | | | | |
|---|---|---|---|---|---|---|
| | | Triticum* aestivum | Galeopsis spp. | Lamium ampl. | Mercurialis annua | Stellaria media |
| 166 | 2.0 | 0 | 100 | 100 | 100 | 100 |
| 204 | 2.0 | 0 | 100 | 100 | 98 | 100 |

"Vuka" variety

We claim:

1. A process for combatting the growth of unwanted plants, wherein the plants or the soil in which they are located are treated with a herbicidally effective amount of an azolylacetophenone ether of the formula I

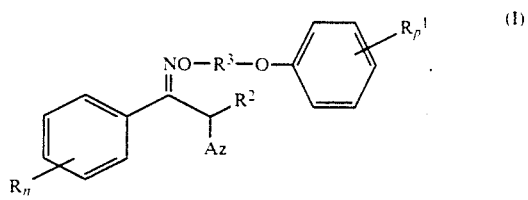

where R and $R_1$ independently of one another are each hydrogen, halogen, alkyl of 1-5 carbons, cyclohexyl, alkoxy of 1-2 carbons, alkylthio of 1-2 carbons, alkylsulfonyl of 1-4 carbons, haloalkyl of 1-4 carbons and 1-5 halogen atoms, nitro, cyano, unsubstituted or substituted phenyl or unsubstituted or substituted phenoxy, $R^2$ is hydrogen or alkyl of 1-4 carbons, $R^3$ is a divalent radical of the formula $-(CH_2)_m-$, $-(CH_2-CH_2O-)_uCH_2CH_2-$, $-(CH_2)CH=CH-(CH_2)-$ or $-(CH_2)C\equiv C-(CH_2)-$, n, p or u independently of one another are each 1, 2 or 3, m is an integer from 2 to 10 and Az is 1,2,4-triazol-1-yl, pyrazol-1-yl or imidazol-1-yl, or their salts or metal complexes.

2. A process according to claim 1, wherein R and $R^1$ in formula I independently of one another are fluorine, chlorine, bromine, $C_1-C_5$-alkyl, methoxy, ethoxy, methylthio, ethylthio, $C_1-C_3$-haloalkyl of a maximum of 5 fluorine or chlorine atoms, substituted or unsubstituted phenyl or substituted or unsubstituted phenoxy, $R^2$ is hydrogen, $R^3$ is $-(CH_2)_m-$, n and p are each 1, m is 2, 3 or 4, and Az is 1,2,4-triazol-1-yl.

3. A process according to claim 2, with the proviso that $R^3$ is $-(CH_2)_m-$ and m is 2.

4. A process for combatting the growth of unwanted plants, wherein the plants or the soil in which they are located are treated with 0,5 to 3 kg/ha of an azolylacetophenone ether herbicide of the formula

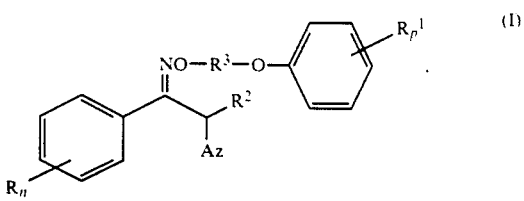

where R and $R_1$ independently of one another are each hydrogen, halogen, alkyl of 1-5 carbons, cyclohexyl, alkoxy of 1-2 carbons, alkylthio of 1-2 carbons, alkylsulfonyl of 1-4 carbons, haloalkyl of 1-4 carbons and 1-5 halogen atoms, nitro, cyano, unsubstituted or substituted phenyl or unsubstituted or substituted phenoxy, $R^2$ is hydrogen or alkyl of 1-4 carbons, $R^3$ is a divalent radical of the formula $-(CH_2)_m-$, $-(CH_2-CH_2O-)_uCH_2CH_2-$, $-(CH_2)CH=CH-(CH_2)-$ or $-(CH_2)C\equiv C-(CH_2)-$, n, p or u independently of one another are each 1, 2 or 3, m is an integer from 2 to 10 and Az is 1,2,4-triazol-1-yl, pyrazol-1-yl or imidazol-1-yl, or their salts or metal complexes.

* * * * *